(12) United States Patent
Davies et al.

(10) Patent No.: US 6,613,551 B2
(45) Date of Patent: Sep. 2, 2003

(54) ENZYMATIC ESTERIFICATION PROCESS

(75) Inventors: Christine Davies, Sharnbrook (GB); Alasdair Robin Macrae, Sharnbrook (GB)

(73) Assignee: Unilever Patent Holdings BV, Vlaardingen (NL)

( * ) Notice: Subject to any disclaimer, the term of this patent is extended or adjusted under 35 U.S.C. 154(b) by 127 days.

(21) Appl. No.: 09/886,019

(22) Filed: Jun. 22, 2001

(65) Prior Publication Data

US 2001/0044140 A1 Nov. 22, 2001

Related U.S. Application Data

(63) Continuation of application No. 09/202,583, filed as application No. PCT/EP97/02959 on May 30, 1997.

(30) Foreign Application Priority Data

Jun. 18, 1996 (EP) .............................. 96304502
May 30, 1997 (WO) ............................... PCT/EP97/02959

(51) Int. Cl.[7] .............. C12P 7/62; C12P 7/00; C12P 7/64; C12Q 1/34; C12N 9/14
(52) U.S. Cl. .................. 435/135; 435/18; 435/132; 435/134; 435/155; 435/195; 435/196; 435/197; 435/69.1
(58) Field of Search ................... 435/195, 196, 435/197, 69.1, 18, 135, 132, 155, 134

(56) References Cited

U.S. PATENT DOCUMENTS

| | | | |
|---|---|---|---|
| 5,191,071 A | 3/1993 | Kirk et al. | 536/4.1 |
| 5,270,188 A | 12/1993 | Yamaguchi et al. | 435/134 |

FOREIGN PATENT DOCUMENTS

| | | |
|---|---|---|
| EP | 0 407 959 A2 | 1/1991 |
| WO | WO 86/05186 | 9/1986 |
| WO | WO 94/21805 | 9/1994 |

OTHER PUBLICATIONS

Dennis et al, Phytochemistry, 13:2469–2473 (1974).
Andrews et al, Biochem. J., 252:199–205 (1988).
Galliard, Biochem. J., 121:379–390 (1971).

*Primary Examiner*—Rebecca E. Prouty
*Assistant Examiner*—Delia Ramirez
(74) *Attorney, Agent, or Firm*—Morgan, Lewis & Bockius LLP

(57) ABSTRACT

Aliphatic, saturated or unsaturated, straight or branched chain C2–C24 monocarboxylic acids and polyhydric alcohols, particularly glycerol are selectively reached to monoesters in the presence of an enzyme which comprises potato lipid acyl hydrolase. The process can be used too for upgrading technical monoglycerides which contain free fatty acids.

10 Claims, 2 Drawing Sheets

ENZYMATIC ESTERIFICATION PROCESS

This is a Continuation National application Ser. No. 09/202,583 filed Dec. 17, 1998 now U.S. Pat. No. 6,274,357 International Application No. PCT/EP97/02959 filed May 30, 1997 which designated the U.S.

The present invention relates to a process for the preparation of mono-esters of aliphatic, saturated or unsaturated, straight or branched chain monocarboxylic acids having from 2 to 24 carbon atoms and polyhydric alcohols in the presence of an acyl hydrolase.

When a carboxylic acid and a polyol are contacted for an esterification process, a mixture is formed comprising fully esterified polyol and polyols partially esterified to various degrees: monoesters, diesters etc. It has appeared very difficult to obtain selectively mono-esters when various hydroxyl groups on the polyol are available for reaction.

BACKGROUND ART

There have been many investigations in the past for developing a convenient method for the selective preparation of mono-esters of polyols. Both enzymatically catalysed as well as non-enzymatically catalysed methods have been investigated. A review of the various ways in which this subject was investigated using enzymatically catalysed processes is given by U. T. Bornscheuer in "Enzyme and Microbial Technology", 17, 578–586, 1995.

An example of such a process, using enzymes having esterase activity, such as lipases or esterases, is given in European Patent Specification EP-B-0,215,038 (Novo Industri A/S). In this patent a process for the preparation of monoglycerides has been described in which first two hydroxyl groups of glycerol are blocked by converting them into a ketal or an acetal, such as isopropylidene glycerol or glycerol diethylketal. This ketal or acetal is then reacted with a carboxylic acid or a carboxylic acid ester in the presence of an esterase. The acetal or ketal protecting group is then removed by acid catalysis from the resulting ester to produce monoglyceride. This synthesis constitutes a rather cumbersome route, however, in that first two adjacent hydroxyl groups of the glycerol molecule need to be blocked involving chemical reaction and the blocking group has then to be removed in a final deprotection step.

Therefore, there is still a need for a simple enzymatic process for preparing fatty acid mono-esters of polyhydric alcohols which is economically attractive with regard to the price of the enzyme and which leads to high yields of monoglyceride and the smallest possible amount of di-esters or higher esters.

A group of closely related glycoproteins, known as patatin, is responsible for lipid acyl hydrolase activity found in potato tubers. The lipid acyl hydrolase is only known for its activity to catalyze the deacylation (hydrolysis) of a range of naturally occurring lipids, e.g. monoglycerides, diglycerides and phospholipids (Biochem. J. 121 (3), 379–390 (1971)).

The use of a lipid acyl hydrolase for the formation of wax esters from long chain monocarboxylic acids and long chain monohydric alcohols has been demonstrated (S. Dennis and T. Galliard, Phytochemistry 13 [11], 2469–2473 [1974]). It is surprising that the synthesis of polyol mono-esters, such as monoglycerides, has never been suggested or proposed.

SUMMARY OF THE INVENTION

We have found that a lipid acyl hydrolase occurring inter alia in potato tubers, is particularly suitable for the enzymatic production of mono-esters of aliphatic carboxylic acids and polyhydric alcohols. This enzyme is available in good quantities, because it can relatively easily be obtained from abundantly available raw materials. Although the tubers contain the highest amount of said enzyme, lesser amounts can also be found in other parts of the potato plant. The enzyme can also be obtained by applying genetic engineering techniques.

Therefore the present invention relates to a process for the preparation of mono-esters of aliphatic, saturated or unsaturated, straight or branched chain C2–C24 monocarboxylic acids and polyhydric alcohols in the presence of an enzyme, wherein the enzyme is potato lipid acyl hydrolase, which means that the hydrolase is obtainable from potatoes or is identical in substrate specificity. Said enzyme selectivity catalyzes the formation of mono-glycerides. Higher esters are formed too, but in very small quantities only.

DETAILS OF THE INVENTION

Figure 1:
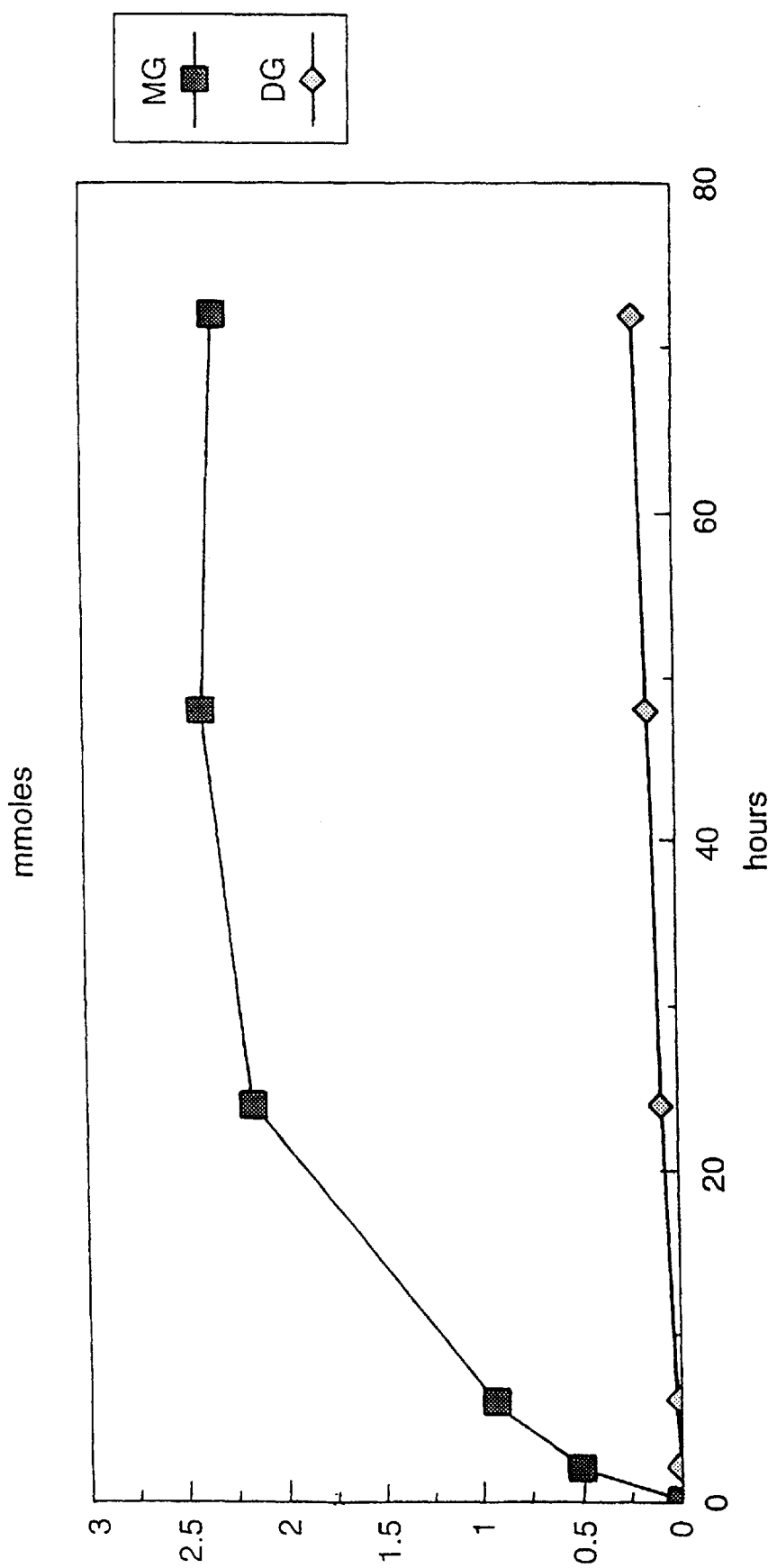
FIG. 1 shows the increase of acylglycerol content when the enzymatic esterification of carboxylic acid and polyol proceeds. MG is monoglyceride, DG is diglyceride. Temperature is 40° C., water content is 3.3 wt. %.

Preferably aliphatic saturated straight chain monocarboxylic acids having from 6 to 22 carbon atoms are used.

The polyhydric alcohol is selected preferably from the group consisting of dihydric alcohols, such as the glycols, e.g. ethylene glycol, propylene glycol, dipropylene glycol, trihydric alcohols, such as glycerol, tetrahydric alcohols such as diglycerol, pentahydric alcohols, hexahydric alcohols such as the sugar alcohols and further sugars, sugar alkyl ethers, such as the alkyl glycosides, and mixtures thereof. The use of glycerol, diglycerol and $C_1$–$C_{18}$ alkylglycosides, such as ethyl glycoside, is preferred.

The lipid acyl hydrolase according to the invention may be used in the form of a protein extract isolated from potato tubers, which extract may be enriched. A specific acyl hydrolase extracted from potatoes is known as patatin. The protein extract may also be obtained from the potato leaves. The protein may also be obtained using genetic engineering techniques. The genes encoding patatin have been cloned successfully. Hence, the fermentative production of patatin in high yield, using a genetically modified yeast or mould, is also possible.

The total water content of the reaction mixture preferably is kept below 10 wt. %, preferably at 0.01–5 wt. %. According to a preferred option the water formed during the reaction is removed. This can be achieved using any technique known in the art, such as pervaporation and vacuum evaporation.

The reaction temperature is between 10° C. and 90° C., preferably between 25° C. and 55° C.

The process of the present invention is also suitable for the upgrading of technical grade monoglycerides which contain free fatty acids. Therefore another embodiment of the present invention is a process for deacidification of a crude monoglyceride comprising reacting the monoglyceride in the presence of glycerol and a catalytic amount of potato lipid acyl hydrolase under similar conditions as described above.

The enzyme according to the invention may be used effectively in an immobilized form, e.g. supported on diatomaceous earth particles.

The invention is illustrated with the following examples:

EXAMPLE 1

Preparation of Potato Protein Extract

Potato tubers (variety-Sante) (1.8 kg) were washed, peeled and chipped into wedges which were immersed immediately into 0.01 wt. % sodium metabisulphite solution containing 10 wt. % polyvinylpolypyrrolidone (PVPP). After draining off the aqueous mixture and PVPP, the potato wedges were put into plastic bags and frozen at minus 18° C.

An aliquot of the potato wedges (1.6 kg) was then allowed to thaw and homogenised in a Waring blender at 4° C. for 1 minute with 1.5 l of 100 mM sodium phosphate buffer (pH 7.0) containing 0.02 wt. % sodium metabisulphite and 1 wt. % PVPP. The homogenate was filtered through three layers of muslin, and the filtrate was centrifuged at 8,000 g for 30 minutes. The supernatant was dialysed overnight at 4° C. against 10 l of deionised water. The resulting dialysed mixture was centrifuged at 18,000 g for 1 hour and the supernatant was shell frozen and reduced to a volume of about 100 ml using a freeze drier. After thawing the concentrated solution was centrifuged at 18,000 g for 1 hour, and the supernatant shell frozen and freeze dried to give a powder (7.2 g) containing about 50 wt. % protein.

EXAMPLE 2

Monoglyceride Synthesis from Oleic Acid

Mixtures containing oleic acid (90%) (1.41 g=5 mmoles), glycerol (0.56 g=6.1 mmoles), potato protein extract (100 mg) and various amounts of water (0–70 $\mu$l) were stirred in stoppered test tubes at various temperatures (40–60° C.). Samples were taken from the reaction mixtures periodically for analysis by GC and TLC.

A typical progress curve for a reaction run at 40° C. is shown in FIG. 1. The major products of the reactions were monoglycerides (MG) with only low levels of diglycerides (DG). Examination of the final products by TLC showed that no triglycerides were formed.

Table 1 shows the compositions of the products formed after 72 hours reaction at various temperatures and various amounts of water. It also shows the initial reaction rates as calculated from the progress curves. Reaction rates are expressed as micromoles product per minute and per gram of extract. At 40° C. addition of water had little effect on the final product yield, but it caused a slight stimulation in the initial reaction rate. Increasing the reaction temperature raised the initial reaction rate. With 3.3 wt. % of water maximum conversion was observed at 50° C. At 60° C. the initial reaction rate was higher, but the final conversion was lower, which suggests that enzyme inactivation occurred during reaction at this higher temperature. At 50° C. with 3.3 wt. % of water 75% of the oleic acid was converted into an acylglycerols mixture consisting of 96 mole % MG and 4 mole % DG.

In the absence of potato extract the rate of acylglycerol formation was very slow (<0.01 $\mu$mole.min$^{-1}$ per gram of extract at 60° C.).

EXAMPLE 3

Synthesis of Monoolein using Vacuum to Improve the Yield

Figure 2:
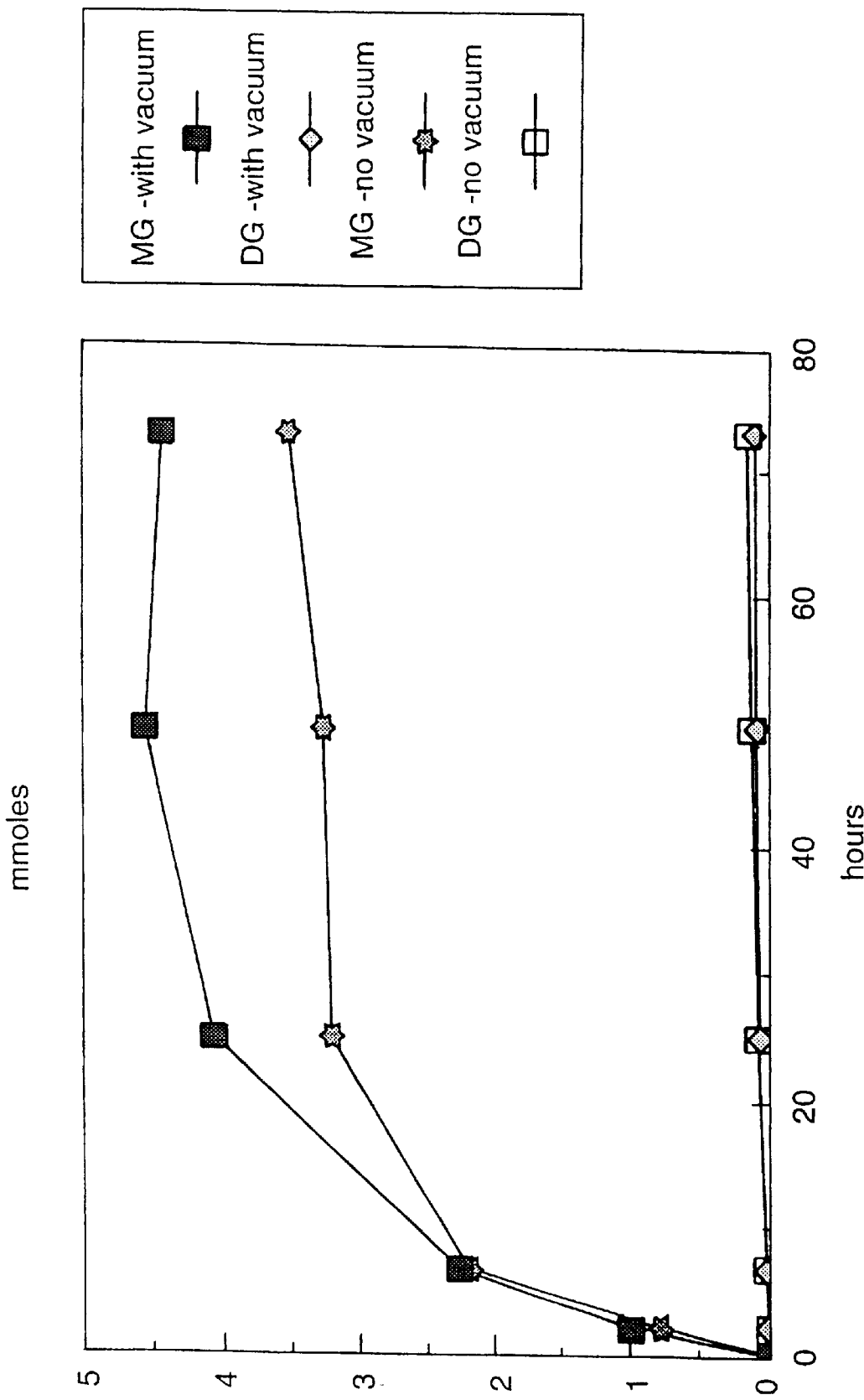
FIG. 2 shows the increase of acylglycerol content when the enzymatic esterification of carboxylic acid and polyol proceeds, with and without the use of vacuum. MG is monoglyceride, DG is diglyceride.

A mixture of oleic acid (1.5 g=5.32 mmoles), glycerol (0.57 g=6.2 mmoles), water (70 $\mu$l) and potato protein extract (100 mg) was stirred at 50° C. and a vacuum (<50 mbar) was applied to the system using an oil pump to remove water from the mixture. For comparison a similar reaction was run without vacuum in a stoppered tube. Samples were taken from the reaction mixtures periodically for analysis by GC. Progress curves for the reactions are given in FIG. 2. In the reaction carried out under vacuum 4.43 mmoles of MG and 0.10 mmoles of DG were formed after 72 hours. 87% of the oleic acid was converted into acylglycerols. In the comparison reaction after 72 hours 3.51 mmoles of MG and 0.14 mmoles of DG were formed. The final conversion of oleic acid into acylglycerols was 71%.

EXAMPLE 4

Synthesis of Monoglycerides from Various Fatty Acids

A mixture of oleic acid (1.45 g=5.14 mmoles), diglycerol (contains 92% diglycerols, 4% glycerol, 4% other polyols (0.9 g), water (70 $\mu$l) and potato protein extract (100 mg) was stirred at 50° C. and a vacuum (<50 mbar) was applied to the system using an oil pump. After 48 hours the reaction was stopped and the products analysed by GC. The major reaction products were diglycerol monoesters (2.60 mmoles). Smaller amounts of diglycerol diesters (0.56 mmoles) and MG (0.18 mmoles) were also formed.

EXAMPLE 5

Preparation of Immobilized Enzyme

Potato protein extract (500 mg) was dissolved in 1.5 ml of phosphate buffer (pH 7.0, 10 mM). Acid washed, flux calcined diatomaceous earth (1.0 g) was added to the protein solution. After mixing a thick paste was obtained. This paste was dried overnight at room temperature in a vacuum oven to give an immobilized enzyme powder.

EXAMPLE 6

Synthesis of Monoglycerides using Immobilized Enzyme Powder

A mixture of oleic acid (1.42 g=5.04 mmoles), glycerol (0.57 g=6.2 mmoles), water (70 $\mu$l) and immobilized enzyme powder (100 mg) was stirred in a stoppered tube at 40° C. for 48 hours. Analysis of the reaction product by GC showed the formation of 3.31 mmoles of monoolein and 0.24 mmoles of diolein. The immobilized enzyme powder has appeared to be an effective catalyst for MG synthesis.

TABLE I

Effect of temperature and amount of added water on monoglyceride and diglyceride synthesis

| Reaction Tempera- ture | Amount of water added | | Initial reaction rate $\mu$moles min$^{-1}$ g extract$^{-1}$ | Products formed after 72 hour reaction | |
|---|---|---|---|---|---|
| | | | | MG | DG |
| (° C.) | ($\mu$l) | (wt. %) | | (mmoles) | (mmoles) |
| 40 | 0 | 0 | 36.4 | 2.34 | 0.09 |
| | 25 | 1.2 | 39.5 | 2.28 | 0.16 |
| | 50 | 2.4 | 44.2 | 2.42 | 0.21 |
| | 70 | 3.3 | 42.5 | 2.34 | 0.21 |
| 50 | 70 | 3.3 | 64.8 | 3.51 | 0.14 |

TABLE I-continued

Effect of temperature and amount of added water on monoglyceride and diglyceride synthesis

| Reaction Temperature (° C.) | Amount of water added (µl) | Amount of water added (wt. %) | Initial reaction rate µmoles min$^{-1}$ g extract$^{-1}$ | Products formed after 72 hour reaction MG (mmoles) | Products formed after 72 hour reaction DG (mmoles) |
|---|---|---|---|---|---|
| 60 | 70 | 3.3 | 110.5 | 2.93 | 0.09 |
| 70 | 70 | 3.3 | — | 0.48 | nd |

EXAMPLE 7

Synthesis of Diol Monoesters of Oleic Acid

Mixtures of oleic acid (7.05 g=25 mmoles), diol (25 mmoles), water (350 µl) and potato protein extract (500 mg) were stirred at 30° C. in stoppered tubes for 6 hours. The resulting reaction mixtures were analysed by gc. The results given in Table III show that monoesters were the major reaction products and only low level of diesters were formed.

TABLE II

Monoglyceride and diglyceride synthesis from various fatty acids

| Fatty acid reactant | Reaction temperatures (° C.) | Products formed after 6 hours reaction MG (mmoles) | Products formed after 6 hours reaction DG (mmoles) |
|---|---|---|---|
| capric (10:0) | 50 | 1.40 | 0.02 |
| lauric (12:0) | 50 | 1.65 | 0.05 |
| myristic (14:0) | 60 | 3.13 | 0.04 |
| palmitic (16:0) | 70 | 0.91 | 0.02 |
| stearic (18:0) | 70 | 0.17 | nd |
| oleic (18:1) | 50 | 1.50 | 0.04 |
| linoleic (18:2) | 50 | 1.59 | 0.03 |
| linolenic (18:3) | 50 | 2.53 | 0.03 |

TABLE III

Synthesis of oleic acid esters of diols

| Diol reactant | Product Formed monoester (mmoles) | Product Formed diester (mmoles) |
|---|---|---|
| ethylene glycol | 6.94 | 0.33 |
| propane-1,3-diol | 9.74 | 0.10 |

EXAMPLE 8

Synthesis of Diglycerol Esters of Oleic Acid

A mixture of oleic acid (1.45 g=5.14 mmoles), diglycerol (ex Unichema International: contains 92% diglycerols, 4% glycerol, 4% other polyols) (0.9 g), water (70 µl) and potato protein extract (100 mg) was stirred at 50° C. and a vacuum (<50 mbar) was applied to the system using an oil pump. After 48 hours the reaction was stopped and the products analysed by GC. The major reaction products were diglycerol monoesters (2.60 mmoles). Smaller amounts of diglycerol diesters (0.56 mmoles) and MG (0.18 mmoles) were also formed.

EXAMPLE 9

Synthesis of Propanediol Monoesters of Capric Acid

Mixtures of capric acid (0.85 g=5 mmoles), and either propan-1,2-diol or propan-1,3-diol (0.38 g=5 mmoles), water (70 µl) and potato protein extract (100 mg) were stirred at 35° C. in stoppered tubes for 24 hours. The reaction products were analysed by GC. With propan-1,2-diol 0.28 mmoles of capric acid monoesters were formed, while with propan-1,3-diol 1.02 mmoles of monoesters were produced. Only low levels of diesters were detected in the reaction products.

EXAMPLE 10

Synthesis of Diglycerol Esters of Capric Acid

A mixture of capric acid (0.86 g=5 mmoles), diglycerol (0.82 g), water (70 µl) and potato protein extract (100 mg) was stirred at 35° C. in a stoppered tube for 8 hours. Analysis of the resulting mixture by GC showed that the major reaction products were capric acid monoesters of diglycerol (1.72 mmoles). Smaller amounts of diglycerol diesters (0.24 mmoles) and monoglycerides (0.11 mmoles) were also formed.

EXAMPLE 11

Synthesis of Ethyl Glucoside Monocaprate

A mixture of capric acid (0.86 g=5 mmoles), ethylglucoside (containing ~80% ethylglucosides, 7% glucose and 10% diglucosides) (1.04 g), water (70 µl) and potato protein extract (100 mg) was stirred at 35° C. in a stoppered tube for 72 hours. Analysis of the resulting reaction mixture by GC showed that 0.21 mmoles of ethylglucoside monocaprate was produced. Only trace amounts of ethylglucoside diesters were detected.

EXAMPLE 12

Synthesis of Sorbitol Esters

A mixture of capric acid (0.86 g=5 mmole), sorbitol (0.91 g=5 mmole), t-butanol (500 µl), water (70 µl) and potato protein extract (100 mg) was stirred at 35° C. in a stoppered tube for 72 hours. Analysis of the resulting reaction mixture showed that sorbitol monocapric (0.12 mmoles) and sorbitol dicaprate (0.04 mmoles) were formed.

What is claimed is:

1. In a process for the preparation of a mono-ester of an aliphatic, saturated or unsaturated, straight or branched chain, C2–C24 monocarboxylic acid and a polyhydric alcohol which comprises contacting the acid and alcohol, in the presence of an enzyme, the improvement wherein the enzyme is potato lipid acyl hydrolase which is not recombinantly produced whereby the mono-ester is formed with a minimum formation of di- or higher-ester.

2. A process according to claim 1 wherein the acid is an aliphatic, saturated, straight chain, C6–C22 monocarboxylic acid.

3. A process according to claim 1 wherein the polyhydric alcohol is selected from the group consisting of dihydric alcohols, trihydric alcohols, tetrahydric alcohols, pentahydric alcohols, hexahydric alcohols, sugars, sugar alkyl ethers and mixtures thereof.

4. A process according to claim 1 wherein the polyhydric alcohol is glycerol or diglycerol.

5. A process according to claim 1 wherein the polyhydric alcohol is an alkylglycoside wherein the alkyl group comprises 1 to 18 carbon atoms.

6. A process according to claim 2 wherein the potato lipid acyl hydrolase is patatin.

7. A process according to claim 1 wherein the potato lipid acyl hydrolase is present in a protein extract isolated from potato tubers.

8. A process according to claim 1 wherein the total water content of the reaction mixture is less than 10% by weight.

9. A process according to claim 1 wherein the reaction temperature is one within the range of 10° C. to 90° C. wherein the enzyme is not deactivated.

10. In a process for the preparation of a mono-ester of an aliphatic, saturated or unsaturated, straight or branched chain, C2–C24 monocarboxylic acid and glycerol which comprises contacting the acid and glycerol, in the presence of an enzyme, the improvement wherein the enzyme is potato lipid acyl hydrolase whereby the mono-ester of glycerol is formed with a minimum formation of di- or higher-ester.

* * * * *